United States Patent
Harmalker et al.

(10) Patent No.: US 9,861,565 B2
(45) Date of Patent: Jan. 9, 2018

(54) CLEANSING COMPOSITION

(71) Applicant: Colgate-Palmolive Company, New York, NY (US)

(72) Inventors: Subhash Harmalker, Somerset, NJ (US); Emma Alvarado, Somerville, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/646,850

(22) PCT Filed: Dec. 4, 2012

(86) PCT No.: PCT/US2012/067764
§ 371 (c)(1),
(2) Date: May 22, 2015

(87) PCT Pub. No.: WO2014/088554
PCT Pub. Date: Jun. 12, 2014

(65) Prior Publication Data
US 2015/0305997 A1    Oct. 29, 2015

(51) Int. Cl.
| | | |
|---|---|---|
| *A61K 8/39* | (2006.01) | |
| *A61K 8/41* | (2006.01) | |
| *A61K 8/42* | (2006.01) | |
| *A61K 8/44* | (2006.01) | |
| *A61K 8/46* | (2006.01) | |
| *A61K 8/86* | (2006.01) | |
| *A61Q 19/10* | (2006.01) | |
| *A61K 8/36* | (2006.01) | |

(52) U.S. Cl.
CPC .............. *A61K 8/39* (2013.01); *A61K 8/361* (2013.01); *A61K 8/416* (2013.01); *A61K 8/42* (2013.01); *A61K 8/442* (2013.01); *A61K 8/463* (2013.01); *A61K 8/86* (2013.01); *A61Q 19/10* (2013.01)

(58) Field of Classification Search
CPC .................................. A61K 8/39; A61Q 19/10
USPC ......................................................... 510/158
See application file for complete search history.

(56) References Cited

U.S. PATENT DOCUMENTS

| | | | |
|---|---|---|---|
| 4,181,633 A | 1/1980 | Colodney et al. | |
| 4,812,253 A | 3/1989 | Small et al. | |
| 5,284,598 A * | 2/1994 | Subramanyam | C11D 3/2079 510/153 |
| 5,308,526 A | 5/1994 | Dias et al. | |
| 5,908,617 A | 6/1999 | Moore et al. | |
| 6,113,892 A * | 9/2000 | Newell | A61K 8/442 424/401 |
| 6,395,692 B1 * | 5/2002 | Jaworski | A61K 8/463 510/141 |
| 6,699,824 B1 | 3/2004 | Dawson et al. | |
| 6,846,787 B1 | 1/2005 | Farrell et al. | |
| 7,700,530 B2 | 4/2010 | Mundschau et al. | |
| 8,168,682 B2 | 5/2012 | O'Connor et al. | |
| 2002/0032241 A1 * | 3/2002 | Schnyder | C11D 3/2034 514/717 |
| 2003/0069317 A1 * | 4/2003 | Seitz, Jr. | A01N 31/08 514/731 |
| 2006/0079419 A1 | 4/2006 | Wagner et al. | |
| 2006/0183662 A1 | 8/2006 | Crotty et al. | |
| 2006/0281652 A1 * | 12/2006 | Keenan | A61K 8/0208 510/141 |
| 2007/0009463 A1 * | 1/2007 | Niebauer | A61K 8/0237 424/70.7 |
| 2008/0014224 A1 | 1/2008 | Boyd et al. | |
| 2009/0325837 A1 | 12/2009 | Mundschau et al. | |
| 2010/0040563 A1 | 2/2010 | Haught | |
| 2011/0118162 A1 * | 5/2011 | Shiloach | A61K 8/361 510/123 |
| 2015/0305997 A1 * | 10/2015 | Harmalker | A61K 8/42 510/158 |

FOREIGN PATENT DOCUMENTS

| | | | |
|---|---|---|---|
| CN | 1438872 | 8/2003 | |
| EP | 1344519 | 9/2003 | |
| EP | 1580259 | 9/2005 | |
| EP | 1074247 | 9/2006 | |
| JP | WO 9913823 A2 * | 3/1999 | ............ A61K 8/342 |
| WO | WO 97/27279 | 7/1997 | |
| WO | WO 97/38672 | 10/1997 | |
| WO | WO 98/14559 | 4/1998 | |
| WO | WO 99/13823 | 3/1999 | |
| WO | WO 99/13833 | 3/1999 | |
| WO | WO 9913833 A1 * | 3/1999 | ............ A61K 8/342 |
| WO | WO 00/42985 | 7/2000 | |
| WO | WO 00/50549 | 8/2000 | |
| WO | WO 2010/001287 | 1/2010 | |
| WO | WO 2011/057909 | 5/2011 | |

OTHER PUBLICATIONS

International Search Report and Written Opinion in International Application No. PCT/US2012/067764, dated Oct. 16, 2013.
Editing Group, China Light Industry Press, Handbook of Daily Chemical Materials (2nd Edition), Dec. 1994, p. 92.

* cited by examiner

*Primary Examiner* — Nicole M Buie-Hatcher
*Assistant Examiner* — M. Reza Asdjodi

(57) ABSTRACT

Described herein are liquid cleansing compositions having a reduced slippery skin feel comprising a) surfactants comprising (i) an alkali metal or ammonium alkyl ether sulfate, (ii) a betaine surfactant and (iii) a fatty acid amide; and b) polyethylene glycol.

13 Claims, No Drawings

CLEANSING COMPOSITION

BACKGROUND OF THE INVENTION

Shower gels, body washes, cleansing lotions, and liquid soaps (hereinafter referred to collectively as "liquid cleansing compositions" irrespective of whether they are liquids, gels, lotions or foams), have grown increasingly popular in recent times. Such compositions typically comprise a mixture of surfactants as skin cleansing agents. The performance of these compositions may be modified by altering the interaction of the surfactants in the mixed surfactant system.

Existing shower gels, body washes, cleansing lotions, and liquid soaps, produce lather and leave a 'slippery' feel on the skin during rinsing and after rinsing. This slippery feel is perceived as an indicator of moisturization in regions such as North America and Europe. Bar soap, on the other hand, does not produce as much lather, but rinses off quickly and leaves a 'squeaky clean' feel. In regions where the use of bar soap is predominant, such as in Asia and Latin America, the slippery feel is perceived as difficult to clean and is undesirable.

It would be desirable to provide a liquid cleansing composition that is acceptable to bar soap users. In particular, it would be desirable to produce a liquid cleansing composition that has a reduced slippery feel on the skin without compromising lather production, such that it is perceived as quick to rinse as bar soaps.

BRIEF SUMMARY OF THE INVENTION

In a first aspect, the present invention provides an aqueous cleansing composition comprising:
a) surfactants comprising (i) an alkali metal or ammonium alkyl ether sulfate, (ii) a betaine surfactant and (iii) a fatty acid amide; and
b) polyethylene glycol.

Typically, the polyethylene glycol has a molecular weight of from 400 Da to 8000 Da. Optionally, the polyethylene glycol has a molecular weight of from 400 Da to 3600 Da, 600 Da to 2000 Da or 1000 Da to 1500 Da. Still further optionally, the polyethylene glycol has a molecular weight of 1450 Da.

Typically, the polyethylene glycol is present in an amount of 0.5 wt. % to 3 wt. %, by total weight of the composition. Optionally, the polyethylene glycol is present in an amount of 1 wt. % to 2 wt. %, by total weight of the composition.

Typically, the surfactants defined in part (a) are present in a total amount of 5 wt. % to 15 wt. % by total weight of the composition on an active basis. Optionally, the surfactants defined in part (a) are present in a total amount of 7 wt. % to 12 wt. % by total weight of the composition on an active basis. Further optionally, the surfactants defined in part (a) are present in a total amount of 8 wt. % to 10 wt. % by total weight of the composition on an active basis.

Typically, the alkali metal of the alkali metal alkyl ether sulfate is selected from sodium and potassium.

Optionally, the alkyl group of the alkyl ether sulfate surfactant comprises 8 to 18 carbon atoms. Further optionally, the alkyl group of the alkyl ether sulfate surfactant comprises 12 to 16 carbon atoms. Still further optionally, the alkyl ether sulfate surfactant has an average degree of ethoxylation of 1 to 6 moles of ethylene oxide per mole, or 2 to 3 moles of ethylene oxide per mole.

Typically, the alkyl ether sulfate surfactant comprises sodium lauryl ether sulfate.

Optionally, the alkali metal or ammonium alkyl ether sulfate surfactant is present in an amount of 5 wt. % to 9 wt. % by total weight of the composition on an active basis. Further optionally, the alkali metal or ammonium alkyl ether sulfate surfactant is present in an amount of 7 wt. % to 8 wt. % by total weight of the composition on an active basis.

Typically, the betaine surfactant comprises cocamidopropyl betaine.

Optionally, the betaine surfactant is present in an amount of 0.5 wt. % to 3.5 wt. % by total weight of the composition on an active basis. Further optionally, the betaine surfactant is present in an amount of 1 wt. % to 2 wt. % by total weight of the composition on an active basis.

Typically, the fatty acid amide surfactant is selected from mono- or di-ethanolamides of linoleic acid, palmitic acid and coconut oil. Optionally, the fatty acid amide surfactant comprises cocomonoethanol amide.

Typically, the fatty acid amide surfactant is present in an amount of 0.1 wt. % to 1 wt. % by total weight of the composition on an active basis. Optionally, the fatty acid amide surfactant is present in an amount of 0.3 wt. % to 0.5 wt. % by total weight of the composition on an active basis.

Optionally, the composition comprises a fatty acid soap. Optionally, the fatty acid soap comprises a neutralized stearic acid and lauric acid. Further optionally, the fatty acid soap comprises at least one of triethanolamine stearate, triethanolamine laurate, sodium stearate, and sodium laurate.

Optionally, the fatty acid soap is present in an amount of 0.1 wt. % to 1 wt. % by total weight of the composition on an active basis. Further optionally, the fatty acid soap is present in an amount of 0.4 wt. % to 0.6 wt. % by total weight of the composition on an active basis.

Optionally, the composition further comprises lauramidopropylamine oxide. Further optionally, the lauramidopropylamine oxide is present in an amount of from 0.1 wt. % to 1 wt. % by total weight of the composition on an active basis.

Optionally, the composition further comprises at least one agent selected from dyes, fragrances, pH adjusters, preservatives, thickeners, viscosity modifiers, buffering agents, antioxidants, chelating agents, opacifiers, humectants and antimicrobial agents.

Further optionally, the composition is in the form of a body wash, shower gel or a liquid soap.

In a second aspect, the present invention provides a method comprising applying the composition to skin, cleansing the skin, and optionally, rinsing the skin, wherein the liquid composition comprises:

Typically, the method further comprises reducing a slippery skin feel.

In a third aspect, the present invention provides a use of polyethylene glycol, optionally having a molecular weight of from 400 Da to 8000 Da, in an aqueous cleansing composition, to reduce slippery skin feel, wherein the liquid cleansing composition additionally comprises an alkali metal or ammonium alkyl ether sulfate surfactant, a betaine surfactant, and a fatty acid amide surfactant.

The present inventors have unexpectedly found that when polyethylene glycol is combined with a surfactant mixture comprising an alkali metal or ammonium alkyl ether sulfate, a betaine, and a fatty acid amide, the slippery skin feel otherwise perceived in the absence of polyethylene glycol, is significantly reduced. Moreover, the reduction in slippery skin feel is achieved without any significant reduction in lather production. Furthermore, the present inventors have found that the reduction in slippery skin feel affected by polyethylene glycol is even more enhanced in the presence of soap. Again, the enhanced reduction in slippery skin feel is achieved without any significant reduction in lather production.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

It should be understood that the detailed description, and specific examples, while indicating embodiments of the invention, are intended for purposes of illustration only and are not intended to limit the scope of the invention.

In some embodiments, the present invention provides an aqeuous cleansing composition comprising:
a) surfactants comprising an alkali metal or ammonium alkyl ether sulfate surfactant, a betaine surfactant, and a fatty acid amide surfactant; and
b) polyethylene glycol.

Cleansing compositions in the context of the present invention include liquids, gels, lotions and foams.

Alkyl ether sulfates surfactants present in the composition of the present invention may have the general formula $RO(C_2H_4O)_xSO_3M$, wherein:
R is an alkyl group of from 6 to 24 carbon atoms, or from 8 to 18 carbon atoms, or from 12 to 16 carbon atoms;
x is 1 to 10, or 1 to 6, or 2 to 3; and
M is a water-soluble cation such as ammonium, sodium, or potassium.

The alkyl ether sulfates may be made as condensation products of ethylene oxide and monohydric alcohols having from 6 to 24 carbon atoms, or from 8 to 18 carbon atoms, or from 12 to 16 carbon atoms. The condensation products are subsequently sulphated and neutralized by methods known to the person skilled in the art. The alcohols may be derived from fats (e.g., coconut oil or tallow), or they may be synthetic. Lauryl alcohol and straight chain alcohols derived from coconut oil are preferred herein. Such alcohols are reacted with 1 to 10, or with 1 to 6, or with 2 to 3, molar proportions of ethylene oxide. Accordingly, the resulting alkyl ether sulfate surfactants may have an average degree of ethoxylation of 1 to 10, or 1 to 6, or 2 to 3 moles of ethylene oxide per mole.

Specific examples of alkyl ether sulfates include sodium and ammonium salts of coconut alkyl triethylene glycol ether sulfate, tallow alkyl triethylene glycol ether sulfate, and tallow alkyl hexaoxyethylene sulfate. A particularly preferred alkyl ether sulfate is sodium lauryl ether sulfate.

In some embodiments, at least one alkyl ether sulfate surfactant is present in the composition in an amount of up to 14 wt. %. In other embodiments, the alkyl ether sulfate surfactant is present in the composition in an amount of from 4 wt. % to 12 wt. %, or from 5 wt. % to 9 wt. % by total weight of the composition on an active basis. Optionally, the alkyl ether sulfate surfactant is present in the composition in an amount of 5 wt. % to 6 wt. %, or 7 wt. %, or 8 wt. % by total weight of the composition on an active basis. Preferably, the alkyl ether sulfate surfactant is present in the composition in an amount of 7 wt. % to 8 wt. % or to 9 wt. % by total weight of the composition on an active basis. Still preferably, the alkyl ether sulfate surfactant is present in the composition in an amount of 7.1 wt. %, or 7.2 wt. % or 7.3 wt. % or 7.4 wt. %, to 7.5 wt. %, or 7.6 wt. %, or 7.7 wt. % or 7.8 wt. % or 7.9 wt. % or 8 wt. % or 8.5 wt. % by total weight of the composition on an active basis.

Examples of betaine surfactants include, but are not limited to, one or combinations of cocodimethylcarboxymethylbetaine, cocamidopropylbetaine, lauryldimethylcarboxymethylbetaine, lauryldimethylcarboxyethylbetaine, cetyldimethyl-carboxymethylbetaine, lauryl-bis-(2-hydroxyethyl)-carboxymethylbetaine, oleyl-dimethylgammacarboxypropylbetaine, and lauryl-bis-(2-hydroxypropyl)-carboxyethyl-betaine. In preferred embodiments, the betaine surfactant comprises cocamidopropyl betaine.

In some embodiments, at least one betaine surfactant is present in the composition in an amount of up to 4 wt. %. In other embodiments, the betaine surfactant is present in the composition in an amount of from 0.5 wt. % to 3.5 wt. % by weight of the composition on an active basis. In yet other embodiments, the betaine surfactant is present in the composition in an amount of from 1 wt. %, or 1.5 wt. % to 2 wt. % or 2.5 wt. % by total weight of the composition on an active basis. Preferably, the betaine surfactant is present in the composition in an amount of 1 wt. % to 2 wt. % by total weight of the composition on an active basis. Still preferably, the betaine surfactant is present in the composition in an amount of 1.1 wt. %, or 1.2 wt. % or 1.3 wt. % or 1.4 wt. %, to 1.5 wt. %, or 1.6 wt. %, or 1.7 wt. % or 1.8 wt. % or 1.9 wt. % or 2 wt. % by total weight of the composition on an active basis.

Fatty acid amide surfactants may include, but are not limited to, primary alkyl amides, alkyl monoalkanol amides, and alkyl diethanolamides. The alkyl moieties may have from 8 to 20 carbon atoms, or from 12 to 16 carbon atoms. In preferred embodiments, the fatty amide surfactant is selected from mono- or di-ethanolamides of linoleic acid, palmitic acid and coconut oil. A highly preferred fatty acid amide is cocomonoethanol amide.

In some embodiments, one or more fatty acid amide surfactants are present in the composition in an amount of 0.05 wt. % to 2 wt. % by total weight of the composition on an active basis. Optionally, the fatty acid amide surfactants are present in the composition in an amount of 0.1 wt. % to 1 wt. % by total weight of the composition on an active basis. In certain embodiments, the fatty acid amide surfactants are present in the composition in an amount of 0.2 wt. %, or 0.3 wt. %, or 0.4 wt. % to 0.5 wt. %, or 0.6 wt. %, or 0.7 wt. %, or 0.8 wt. %, or 0.9 wt. % or 1 wt. % by total weight of the composition on an active basis. In a preferred embodiment, the fatty acid amide surfactants are present in the composition in an amount of 0.3 wt. % to 0.5 wt. % by total weight of the composition on an active basis.

The surfactants comprising the alkali metal or ammonium alkyl ether sulfate surfactant, betaine surfactant, and fatty acid amide surfactant may be present in a total amount of 5 wt. % to 15 wt. % by total weight of the composition, or in a total amount of 7 wt. % to 12 wt. % by total weight of the composition, on an active basis. In some embodiments, the surfactants comprising the alkali metal or ammonium alkyl ether sulfate surfactant, the betaine surfactant, and fatty acid amide are present in a total amount of 6 wt. %, or 7 wt. % or 8 wt. %, to 9 wt. %, or 10 wt. %, or 11 wt. %, or 12 wt. %, by total weight of the composition on an active basis. In other embodiments, the surfactants comprising the alkali metal or ammonium alkyl ether sulfate surfactant, the betaine surfactant, and fatty acid amide are present in a total amount of 8 wt. % to 10 wt. % by total weight of the composition, on an active basis.

In some embodiments, the composition does not comprise any additional surfactants.

The present inventors have surprisingly found that the incorporation of polyethylene glycols (PEGs) (also known as polyoxyethylenes) into a surfactant mixture comprising an alkyl ether sulfate, a betaine, and a fatty acid amide, reduces the slippery skin feel that is otherwise experienced, whilst maintaining foam production.

Low or medium molecular weight polyethylene glycols having a molecular weight of from 400 Da to 8000 Da are preferred. For example, one or more of PEG 400, PEG 600, PEG 800, PEG 1000, PEG 1200, PEG 1400, PEG 1600, PEG 1800, PEG 2000, PEG 2200, PEG 2400, PEG 2600, PEG 2800, PEG 3000, PEG 3200, PEG 3400 and PEG 3600 may be usefully incorporated into the compositions of the present invention. (The numbers refer to the molecular weight of the polyethylene glycol.)

In some embodiments, the polyethylene glycol has as molecular weight of from 400 Da to 3600 Da, or from 600 Da to 2600 Da, or from 600 Da to 2000 Da, or from 1000 Da to 1500 Da. In one embodiment, PEG 600 is used. In another embodiment, PEG 1450 is used.

The polyethylene glycol may be present in an amount of 0.5 wt. % to 3 wt. %, by total weight of the composition. In preferred embodiments, the polyethylene glycol is present in the composition in an amount of 0.5 wt. % to 3 wt. %, or 0.5 wt. % to 2.5 wt. %, or 1 wt. % to 2 wt. %, by total weight of the composition. In more preferred embodiments, the polyethylene glycol is present in an amount of about, 1.1 wt. %, or 1.2 wt. %, or 1.3 wt. %, or 1.4 wt. % to 1.5 wt. %, or 1.6 wt. %, or 1.7 wt. %, or 1.8 wt. %, or 1.9 wt. % or 2 wt. % by total weight of the composition.

In some embodiments, the composition of the present invention further comprises a fatty acid soap.

The term "soap" as used herein may be defined as the alkali metal or alkanol ammonium salts of aliphatic alkane- or alkene-monocarboxylic acids, preferably having 6 to 22 carbon atoms, or 6 to 18 carbon atoms, or 12 to 18 carbon atoms.

The fatty acid soap of the present invention typically comprises a neutralized fatty acid. Typical fatty acids used for soaps include, myristic acid, lauric acid, palmitic acid, and stearic acids. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils.

The fatty acids may be neutralized with any base to form a soap. Typical bases include, but are not limited to, sodium hydroxide, potassium hydroxide, and triethanolamine. In certain embodiments, the fatty acid soap is formed from fatty acids neutralized by two or more bases. In certain embodiments, the bases are sodium hydroxide and triethanolamine. In certain embodiments, the molar ratio of sodium hydroxide and triethanolamine is 1:1. In certain embodiments, the fatty acids are stearic acid and lauric acid. In certain embodiments, the fatty acid soap comprises at least one of triethanolamine stearate, triethanolamine laurate, sodium stearate and sodium laurate.

The soap can be made in situ in the composition by mixing fatty acids with the neutralizing agent. In certain embodiments, the molar amount of fatty acids is greater than the molar amount of neutralizing agent such that fatty acid remains in the composition. In some embodiments, the fatty acid soap is provided in the composition in the form of soap chips.

In some embodiments, the fatty acid soap is present in the composition in an amount of up to 2 wt. %. In other embodiments, the fatty acid soap is present in the composition in an amount of 0.05 wt. % to 2 wt. % by total weight of the composition on an active basis. Optionally, the fatty acid soap is present in the composition in an amount of 0.1 wt. % to 1 wt. % by total weight of the composition on an active basis. Further optionally, the fatty acid soap is present in the composition in an amount of 0.1 wt. %, or 0.2 wt. % or 0.3 wt. % or 0.4 wt. %, to 0.5 wt. %, or 0.6 wt. %, or 0.7 wt. % or 0.8 wt. % or 0.9 wt. % or 1 wt. %. Preferably, the fatty acid soap is present in the composition in an amount of 0.4 wt. % to 0.6 wt. %.

The carrier of the composition comprises water. Water is typically present in the composition in an amount that is sufficient to form a liquid composition. In certain embodiments, the amount of water is at least 65 wt. %, or 65 wt. % to 90 wt. % by total weight of the composition. In other embodiments, the amount of water is 75 wt. % to 85 wt. % by total weight of the composition.

The composition of the present invention may be provided, without limitation, in the form of a body wash, shower gel or a liquid soap.

In some embodiments, the composition further comprises a foaming agent such as lauramidopropylamine oxide. The lauramidopropylamine oxide may be present in an amount of 0.1 wt. % to 1 wt. % by total weight of the composition on an active basis, or in an amount of 0.3 wt. %, or 0.4 wt. % or 0.5 wt. % to 0.6 wt. %, or 0.7 wt. %, or 0.8 wt. %, or 0.9 wt. %, or 1 wt. % by total weight of the composition on an active basis.

The present invention further provides a method comprising applying any of the above described compositions to skin, cleansing the skin, and optionally, rinsing the skin, wherein the composition comprises.

The composition may be as defined herein. The method may further comprise reducing slippery skin feel.

The present invention additionally provides a use of polyethylene glycol, optionally having a molecular weight of from 400 Da to 8000 Da, in a liquid cleansing composition, to reduce slippery skin feel, wherein the liquid cleansing composition further comprises an alkali metal or ammonium alkyl ether sulfate surfactant, a betaine surfactant, and a fatty acid amide surfactant.

A composition comprising polyethylene glycol and a surfactant mixture comprising an alkali metal or ammonium alkyl ether sulfate, a betaine and a fatty acid amide, results in a significantly reduced slippery skin feel. Moreover, the reduction in slippery skin feel is achieved without any significant reduction in lather production. Furthermore, the reduction in slippery skin feel effected by polyethylene glycol is even more enhanced in the presence of soap. Again, the enhanced reduction in slippery skin feel is achieved without any significant reduction in lather production.

EXAMPLES

Example 1—Shower Gel Composition

A typical shower gel composition according to the present invention is illustrated in Table 1. It is referred to as base in the examples.

TABLE 1

| Ingredients | % Activity | Wt. % Active |
|---|---|---|
| DI Water and minors | 100 | Q.S. |
| Coco Mono Ethanol Amide (CMEA) | 95 | 0.4 |
| Sodium lauryl ether sulfate | 70 | 6.9 |
| Polyquaternium 7 | 8 | 0.1 |
| Cocamidopropyl betaine | 30 | 2.1 |

Example 2—Hand Wash Study

A hand wash study was conducted to investigate the effects of polyethylene glycol (PEG), and soap, on foam production and the slippery feel experienced when using a base formulation comprising sodium lauryl ether sulfate, cocamidopropyl betaine, and cocomonoethanol amide. Various formulations, as listed in Table 2, were applied to hands. The amount of foam production and the slippery feel experienced during rinsing was assessed, and given a score. The higher the score for foam production, the greater the amount of foam produced. The higher the score for slippery feel, the more slippery the composition is. The results are indicated in Table 2.

TABLE 2

| Sample | Foam Higher rank more foam | Slippery feel during rinse Higher rank more slippery |
|---|---|---|
| Base | 6 | 7 |
| Base + 0.5 wt. % soap | 3 | 6 |
| Base + 0.5 wt. % soap + 1.2 wt. % PEG400 | 6 | 3 |
| Base + 0.5 wt. % soap + 1.2 wt. % PEG600 | 7 | 5 |
| Base + 0.5 wt. % soap + 1.2 wt. % PEG1450 | 7 | 4 |
| Base + 0.5 wt. % soap + 1.2 wt. % PEG3350 | 7 | 4 |

As can be seen in Table 2, when PEG 400, PEG 600, PEG1450 or PEG 3350, is incorporated into the base formula in combination with soap, the slippery feel is reduced whilst foam production is maintained.

Example 3—Lather Production and Slippery Feel (1)

Various formulations comprising PEG (having a molecular weight of 600 or 1450 Da), and optionally, soap chips, were tested for their ability to generate lather and foam during washing, and were assessed for their skin feel effects during washing and their slippery feel during rinsing. Bar soap, and a base formulation comprising sodium lauryl ether sulfate, cocamidopropyl betaine and cocomonoethanol amide (referred to as Base) acted as negative controls for the experiment. The higher the score for foam/lather production, the greater the amount of foam/lather produced. The higher the score for slippery feel, the more slippery the composition is. In the table, AI is the percent of the surfactant mixture in the composition, SC is soap chip, LMDO is lauramidopropylamine oxide, and the amounts are weight %.

TABLE 3

| Sample | During Wash amount of lather | During Wash amount of foam | During Wash Skin Feel | Slippery during Rinse |
|---|---|---|---|---|
| Bar Soap | 5.6 | 5.6 | 4.2 | 2.2 |
| #15(9.44% AI/0.5% SC/0.5% LMDO/1.2% PEG600) | 7.8 | 7.2 | 7.2 | 2.8 |
| #5(8.22% AI/0.5SC/0.5% LMDO/1.2% PEG1450) | 6.3 | 6.3 | 6.1 | 4.0 |
| #6(9.44% AI/1.0% LMDO/0.5% PEG1450) | 7.6 | 7.8 | 7.8 | 4.0 |
| #7(8.22% AI/1.0% LMDO/0.5% PEG600) | 6.8 | 7.4 | 6.2 | 4.0 |
| #2(8.22% AI/0.5SC/0.5% LMDO/0.5% PEG600) | 6.2 | 6.3 | 6.8 | 4.3 |
| #12(9.44% AI/1.0% LMDO/1.2% PEG600) | 5.8 | 5.8 | 5.8 | 4.6 |
| #13- (9.44% AI/0.5% SC/1% LMDO/1.2% PEG1450) | 6.2 | 6.6 | 6.8 | 4.8 |
| #4(9.44% AI/0.5% LMDO/0.5% PEG600) | 5.2 | 5.3 | 5.7 | 4.8 |
| #10(8.22% AI/0.5% LMDO/0.5% PEG1450) | 6.0 | 5.8 | 6.4 | 5.0 |
| #11(9.44% AI/0.5% LMDO/1.2% PEG1450) | 6.0 | 6.2 | 6.0 | 5.0 |
| #14(8.22% AI/0.5SC/1.0% LMDO/0.5% PEG1450) | 6.4 | 6.8 | 6.6 | 5.0 |
| #3(8.22% AI/0.5SC/1.0% LMDO/1.2% PEG600) | 5.2 | 5.8 | 6.0 | 5.2 |
| #8(8.22% AI/0.5% LMDO/1.2% PEG600) | 6.0 | 5.6 | 5.0 | 5.6 |
| #16- (9.44% AI/0.5% SC/0.5% LMDO/0.5% PEG600) | 5.6 | 5.8 | 6.6 | 5.6 |
| #1-(9.44% AI/.5% SC/1% LMDO/0.5% PEG600) | 5.8 | 5.8 | 6.4 | 6.0 |
| #9(8.22% AI/1.0% LMDO/1.2% PEG1450) | 6.4 | 7.0 | 7.0 | 6.6 |
| Base | 6.6 | 6.0 | 6.0 | 7.0 |

As can be seen in Table 3, as expected, bar soap produced the least slippery feel during rinse, yet also the least amount of lather and foam. The base formulation produced a high amount of lather and foam, yet also the greatest slippery feel.

However, when PEG 600 or PEG 1450 is incorporated into the base formulation (see in particular, test formulations 7 and 6, respectively), the amount of lather and foam generated is maintained, whilst the slippery feel is significantly reduced.

Furthermore, test formulations comprising PEG 600 or PEG 1450 in addition to soap (see in particular, test formulations 15 and 5, respectively), produced acceptable amounts of lather and foam, whilst exhibiting a reduced slippery feel.

Example 4—Lather Production and Slippery Feel Using PEG 600

Various formulations comprising the Base (sodium lauryl ether sulfate, cocamidopropyl betaine and cocomonoethanol amide), PEG 600, and optionally, soap chips, were tested for tested for their ability to generate lather, and were assessed for their slippery feel during rinsing. The formulations were then ranked in order of their efficacy/desirability based on their ability to generate lather and reduce slippery feel. The results are illustrated in Table 4. The higher the score for lather production, the greater the amount of lather produced. The higher the score for slippery feel, the more slippery the composition is. In the table, the amounts for PEG600 level, Soap Chip (SC) level, LMDO, and AI are weight %.

TABLE 4

| | PEG level | SC level | LMDO | AI | LatherAmt | SlipRinse |
|---|---|---|---|---|---|---|
| 1 | 1.2 | 0.66 | 0.5 | 9.44 | 6.86 | 3.68 |
| 2 | 1.2 | 0.66 | 0.5 | 9.43 | 6.86 | 3.68 |
| 3 | 1.2 | 0.66 | 0.5 | 9.44 | 6.86 | 3.69 |
| 4 | 1.2 | 0.66 | 0.5 | 9.38 | 6.86 | 3.73 |
| 5 | 1.2 | 0.66 | 0.52 | 9.44 | 6.79 | 3.68 |
| 6 | 1.2 | 0.66 | 0.5 | 9.27 | 6.86 | 3.82 |
| 7 | 1.2 | 0.66 | 0.5 | 9.17 | 6.86 | 3.90 |
| 8 | 0.5 | 0 | 1 | 8.2 | 7.03 | 4.19 |
| 9 | 0.5 | 0 | 1 | 8.2 | 7.02 | 4.19 |
| 10 | 0.5 | 0 | 1 | 8.2 | 7.01 | 4.19 |
| 11 | 0.5 | 0 | 1 | 8.36 | 7.02 | 4.25 |
| 12 | 0.5 | 0.04 | 1 | 8.2 | 6.98 | 4.24 |
| 13 | 0.5 | 0 | 1 | 8.45 | 7.02 | 4.29 |
| 14 | 0.5 | 0 | 1 | 8.53 | 7.02 | 4.33 |
| 15 | 1.2 | 0.66 | 0.51 | 8.97 | 6.84 | 4.07 |
| 16 | 0.5 | 0 | 1 | 8.58 | 7.02 | 4.35 |
| 17 | 1.2 | 0.66 | 0.5 | 8.85 | 6.86 | 4.17 |
| 18 | 0.5 | 0 | 1 | 8.7 | 7.02 | 4.40 |
| 19 | 0.5 | 0 | 1 | 8.79 | 7.03 | 4.44 |
| 20 | 0.5 | 0 | 1 | 8.85 | 7.02 | 4.46 |
| 21 | 0.5 | 0 | 1 | 8.87 | 7.02 | 4.47 |
| 22 | 1.15 | 0.54 | 0.5 | 9.44 | 6.68 | 4.01 |
| 23 | 0.5 | 0 | 0.92 | 8.2 | 6.76 | 4.19 |
| 24 | 1.2 | 0.66 | 0.5 | 8.64 | 6.86 | 4.35 |
| 25 | 1.2 | 0.66 | 0.5 | 8.61 | 6.86 | 4.37 |
| 26 | 0.5 | 0 | 0.91 | 8.2 | 6.72 | 4.19 |
| 27 | 1.2 | 0.66 | 0.5 | 8.56 | 6.86 | 4.42 |
| 28 | 0.5 | 0.03 | 1 | 9.14 | 7.00 | 4.61 |
| 29 | 0.5 | 0 | 1 | 9.37 | 7.02 | 4.68 |
| 30 | 1.2 | 0.66 | 0.5 | 8.36 | 6.86 | 4.59 |
| 31 | 0.6 | 0 | 1 | 9.4 | 6.92 | 4.73 |
| 32 | 0.5 | 0.08 | 1 | 9.42 | 6.93 | 4.80 |
| 33 | 1.2 | 0.64 | 0.5 | 8.2 | 6.84 | 4.77 |
| 34 | 0.69 | 0 | 1 | 9.44 | 6.82 | 4.77 |
| 35 | 0.94 | 0 | 1 | 9.44 | 6.56 | 4.84 |

As can be seen in Table 4, formulations comprising PEG 600 exhibit reduced slippery feel, whilst maintaining good lather production (see in particular, formulations 8 to 11). Unexpectedly, formulations comprising PEG 600 and soap chips exhibit even more reduced slippery feel whilst maintaining good lather production (see in particular, formulations 1 to 7).

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. An aqueous cleansing composition, comprising:
   a surfactant combination consisting of sodium lauryl ether sulfate, cocamidopropyl betaine, and cocomonoethanol amide;
   a fatty acid soap present in an amount of 0.1 wt % to 1 wt % based on a total weight of the composition on an active basis; and
   polyethylene glycol, wherein the polyethylene glycol is present in an amount of 0.5 wt. % to 1.2 wt. % by total weight of the composition,
   wherein the surfactant combination is present in a total amount of 5 wt % to 15 wt % based on a total weight of the composition on an active basis,
   wherein the sodium lauryl ether sulfate is present in an amount of 5 wt. % to 9 wt. % based on a total weight of the composition on an active basis,
   wherein the cocamidopropyl betaine is present in an amount of 0.5 wt. % to 3.5 wt. % based on a total weight of the composition on an active basis,
   wherein the cocomonoethanol amide is present in an amount of 0.05 wt. % to 2 wt. % based on a total weight of the composition on an active basis, and
   wherein the polyethylene glycol has a molecular weight of from about 400 Da to about 3200 Da.

2. The composition according to claim 1, further comprising a foaming agent, the foaming agent comprising lauramidopropylamine oxide.

3. The composition of claim 1, wherein the composition is in the form of a body wash, shower gel or a liquid soap.

4. A method comprising applying the composition of claim 1 to skin, cleansing the skin, and optionally, rinsing the skin.

5. The composition according to claim 1, wherein the polyethylene glycol has a molecular weight of about 600 Da.

6. The composition according to claim 5, further comprising soap chips, wherein the soap chips comprise the fatty acid soap.

7. The composition according to claim 1, wherein the polyethylene glycol has a molecular weight of from about 600 Da to about 1450 Da.

8. The composition of claim 2, wherein the lauramidopropylamine oxide is present in an amount of 0.3 wt % to 1 wt % based on a total weight of the composition on an active basis.

9. The composition of claim 2, wherein the lauramidopropylamine oxide is present in an amount of 0.4 wt % to 1 wt % based on a total weight of the composition on an active basis.

10. The composition of claim 2, wherein the lauramidopropylamine oxide is present in an amount of 0.5 wt % to 1 wt % based on a total weight of the composition on an active basis.

11. The composition of claim 2, wherein the lauramidopropylamine oxide is present in an amount of 0.5 wt % based on a total weight of the composition on an active basis.

12. The composition of claim 1, wherein the molecular weight of the polyethylene glycol is about 1,450 Da.

13. The composition of claim 1, wherein the surfactant combination is present in a total amount of 8 wt % to 10 wt % based on a total weight of the composition on an active basis.

* * * * *